United States Patent
Rufer et al.

(10) Patent No.: US 9,108,004 B2
(45) Date of Patent: Aug. 18, 2015

(54) AMPOULE UNIT WITH THREAD

(75) Inventors: Thomas Rufer, Ostermundigen (CH); Hanspeter Stoller, Bern (CH); Rolf Burkhalter, Thun (CH); Hanspeter Heiniger, Lotzwil (CH)

(73) Assignee: Roche Diagnostics International AG, Steinhausen (CH)

( * ) Notice: Subject to any disclaimer, the term of this patent is extended or adjusted under 35 U.S.C. 154(b) by 446 days.

(21) Appl. No.: 12/762,828

(22) Filed: Apr. 19, 2010

(65) Prior Publication Data

US 2011/0106018 A1 May 5, 2011

Related U.S. Application Data

(63) Continuation of application No. PCT/EP2008/008677, filed on Oct. 14, 2008.

(30) Foreign Application Priority Data

Oct. 19, 2007 (EP) .................................. 07118924

(51) Int. Cl.
*A61M 5/315* (2006.01)
*A61M 5/24* (2006.01)
*A61M 5/31* (2006.01)

(52) U.S. Cl.
CPC .............. *A61M 5/31586* (2013.01); *A61M 5/24* (2013.01); *A61M 5/3129* (2013.01); *A61M 5/3135* (2013.01); *A61M 5/3137* (2013.01); *A61M 5/31511* (2013.01); *A61M 5/31513* (2013.01); *A61M 2005/31508* (2013.01)

(58) Field of Classification Search
CPC . A61M 5/24; A61M 5/3135; A61M 5/31511; A61M 5/31513; A61M 5/31586; A61M 2005/2433; A61M 2005/2437; A61M 2005/2444; A61M 2005/31508
USPC ......... 604/187, 211, 218, 224, 232, 220, 227, 604/234; 222/390
See application file for complete search history.

(56) References Cited

U.S. PATENT DOCUMENTS

| | | | | |
|---|---|---|---|---|
| 2,165,597 | A | * | 7/1939 | Widoe, Sr. .................... 433/171 |
| 2,475,939 | A | * | 7/1949 | Applezweig .................. 604/201 |
| 3,128,765 | A | * | 4/1964 | Tint .............................. 604/193 |
| 4,189,065 | A | | 2/1980 | Herold |

(Continued)

FOREIGN PATENT DOCUMENTS

| | | |
|---|---|---|
| EP | 1 752 172 A1 | 8/2005 |
| GB | 2 058 228 | 7/1980 |

(Continued)

OTHER PUBLICATIONS

International Search Report, Appln. No. PCT/EP2008/008677 filed Oct. 14, 2008, 4 pgs.

(Continued)

*Primary Examiner* — Kami A Bosworth
(74) *Attorney, Agent, or Firm* — Dinsmore & Shohl LLP

(57) ABSTRACT

Ampoule unit for an administering device, comprising an ampoule having a distal end with an opening for dispensing a product and a proximal end with an opening for accommodating a displacement body unit, and the proximal end of the ampoule has a thread which can be placed in a thread engagement with a complementary thread which is part of the displacement unit or a displacement body unit.

16 Claims, 4 Drawing Sheets

(56) References Cited

U.S. PATENT DOCUMENTS

| | | | |
|---|---|---|---|
| 4,583,974 A * | 4/1986 | Kokernak | 604/211 |
| 5,059,179 A * | 10/1991 | Quatrochi et al. | 604/110 |
| 5,618,273 A | 4/1997 | Fischer | |
| 6,571,992 B2 | 6/2003 | Pierson et al. | |
| 6,957,752 B2 * | 10/2005 | Py et al. | 222/390 |
| 2002/0113088 A1 | 8/2002 | Pierson et al. | |
| 2003/0167093 A1 | 9/2003 | Xu et al. | |

FOREIGN PATENT DOCUMENTS

| | | |
|---|---|---|
| WO | 2004/016303 A1 | 2/2004 |
| WO | 2009/049858 A1 | 4/2009 |

OTHER PUBLICATIONS

PCT Written Opinion of the International Searching Authority, Appln. No. PCT/EP2008/008677 filed Oct. 14, 2008, 7 pgs.

\* cited by examiner

AMPOULE UNIT WITH THREAD

CROSS REFERENCE TO RELATED APPLICATIONS

This application is a continuation of International Application No. PCT/EP2008/008677, filed Oct. 14, 2008, which claims priority to European Patent application EP 07 118 924.5, filed Oct. 19, 2007.

TECHNICAL FIELD

Embodiments of this disclosure relate to an ampoule unit having an ampoule for use with an administering device such as an injection device or a syringe, the ampoule having a threaded opening at its proximal end. Further embodiments relate to an ampoule unit with an ampoule and an adapter. In this case, the ampoule can be connected to the adapter so that it cannot move with respect to the adapter.

BACKGROUND

As background, numerous administering devices are known for dispensing fluids such as, for example, medicaments like insulin, hormone preparations, or other medical or cosmetic substances. With most of these devices, especially if dispensing is performed via a needle coupled to the distal end of the ampoule or device, the fluid is dispensed by a linearly guided plunger. Particularly in the case of low basal rates, static friction problems can occur due to the fact that the stopper or plunger causing the dispensing action (e.g., driven by a plunger rod) also assumes a sealing function and is made from a rubber-like material. In situations where this stopper or plunger is driven forward in a purely linear sliding action, a change between static friction and sliding friction repeatedly occurs between the plunger and the internal wall of the ampoule. This may cause the plunger to exhibit delayed and/or jerky movement when dispensing the fluid. As a result, uniform or consistent dispensing of the fluid from the ampoule unit is not always guaranteed.

SUMMARY

In one embodiment, an ampoule unit for an administering device, comprises an ampoule having a distal end with an opening for dispensing a product and a proximal end with an opening for accommodating a displacement unit, wherein the proximal end of the ampoule has a thread which can be placed in a thread engagement with a complementary thread which is part of the displacement unit.

In another embodiment, an ampoule unit for an administering device comprises an ampoule with a distal end with an opening for dispensing a product and a proximal end with an opening for accommodating a displacement unit and an adapter which can be or is connected to the ampoule so that is not able to move in rotation or translation, wherein the adapter comprises a thread which can be placed in a thread engagement with a complementary thread which is part of a displacement body or the displacement unit.

BRIEF DESCRIPTION OF THE DRAWINGS

The embodiments set forth in the drawings are illustrative and exemplary in nature and not intended to limit the recited inventions defined by the claims. The following detailed description of the illustrative embodiments can be understood when read in conjunction with the following drawings, where like structures are indicated with like reference characters and in which:

LIST OF REFERENCE CHARACTERS

Figure 1:
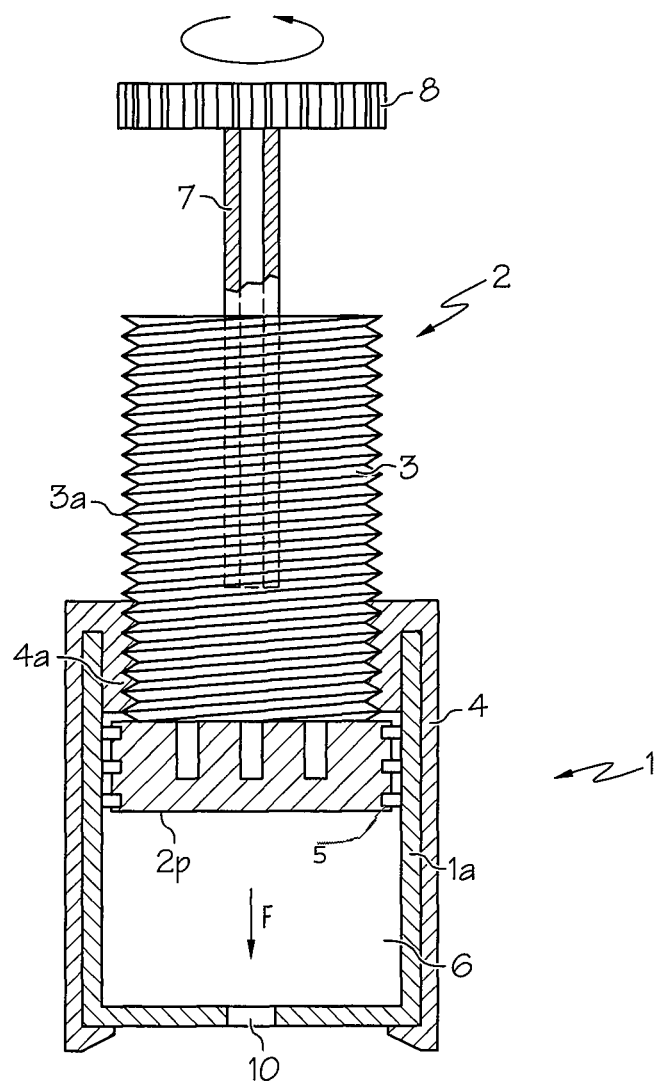
FIG. 1 depicts an ampoule unit according to one or more embodiments shown and described herein.

1 Ampoule unit
1a Ampoule
2 Plunger unit
2a Plunger thread
2b Central plunger rod
2c Plunger sleeve
2d Slot
2p Plunger
3 Plunger rod
3a Plunger rod thread
4 Adapter
4a Adapter thread
5 Seal
6 Fluid chamber
7 Drive element
8 Gear
9 Housing
9a Housing thread
10 Opening
F Forward drive direction

DETAILED DESCRIPTION

The static friction exhibited by the stopper or plunger is particularly problematic if several extremely small quantities are to be dispensed from an ampoule in succession (e.g., in a defined, pre-settable interval of time). If, during such dispensing, the plunger movement is inhibited due to static friction, the amount dispensed may be too small, in spite of the linear forward movement of the plunger rod. During the next dispensing operation, the inhibition of the plunger due to static friction may be overcome, causing the plunger as a whole to travel a greater distance than that intended, which may result in too high a dosage. Consequently, the patient or user may be administered less or more of the fluid substance when administering small doses until the ampoule is completely empty. This problem is obviously magnified when smaller quantities of fluid are to be administered with each application. In an extreme situation, this can lead to switching between dispensing a quantity of zero (i.e., the plunger is completely held back by static friction) and dispensing twice the intended quantity in the next step.

As an example, U.S. Patent Application Publication No. 2003/0167093 A1 describes a pump for dispensing a fluid from a reservoir. The pump comprises a first part for accommodating the reservoir incorporating a plunger unit, for example an ampoule, and a second part for accommodating the motor and the plunger forward drive mechanism. The two parts are disposed adjacent to one another, thereby reducing the length of the pump. A plate fixedly connected to a nut seated on a threaded rod driven in rotation and connected to a motor acts on the rear end of the plunger unit. When the motor rotates, the nut moves in the forward drive direction and pushes the plunger unit via the plate in a linear motion in the direction in which the fluid is dispensed. Alternatively, the threaded rod may be directly connected to the plunger rod via a gear. The plunger rod sits in a thread connection with the plunger and moves it linearly in the forward drive direction.

Figure 4:
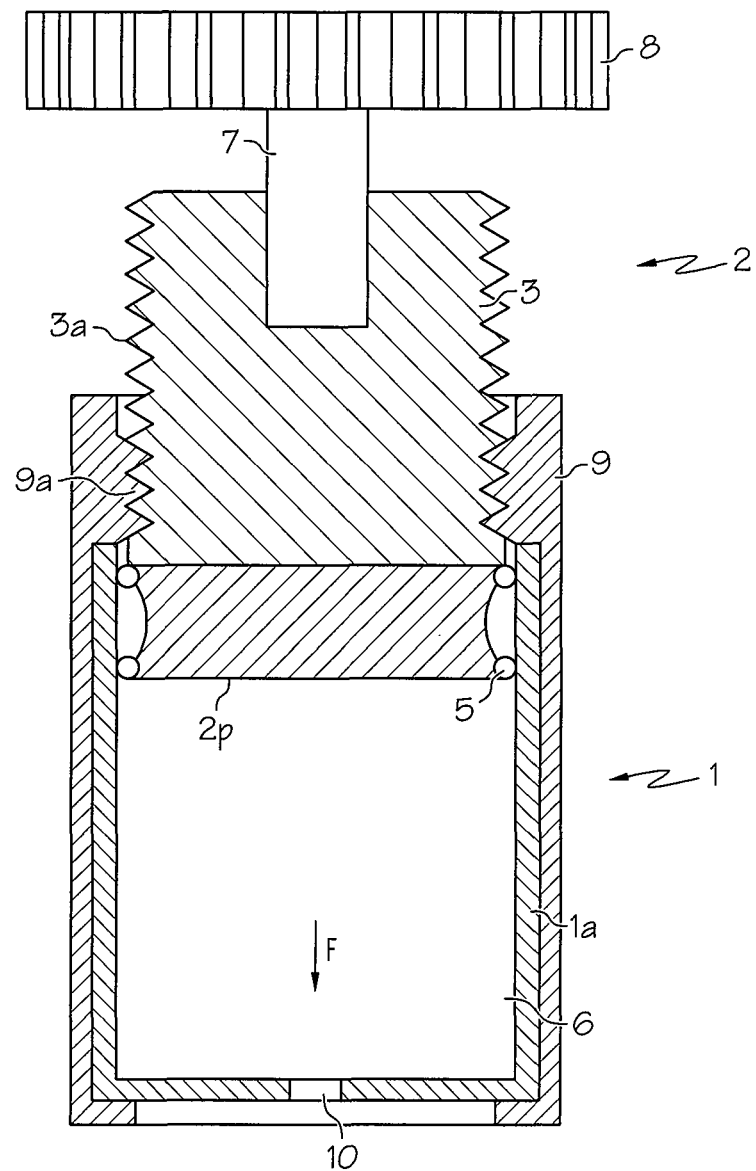
FIG. 4 depicts an ampoule unit according to one or more embodiments shown and described herein.

As another example, European Patent No. EP 1 752 172 A1 discloses a drive mechanism for an infusion pump. As described in paragraph 0030 of this patent, FIG. 4 illustrates an ampoule with an internal thread in which a plunger with an external thread locates, which is thus screwed into the ampoule in a rotating motion about its rotation axis and dispenses the fluid contained in the ampoule as a result. In order to be able to completely empty the ampoule described in this reference, the internal thread must extend across the entire internal length of the ampoule.

Therefore, the objective of this disclosure is to propose an ampoule unit for administering devices which ensures that when repeatedly dispensing a small quantity of liquid from an ampoule, the quantity dispensed is accurate and repeatable.

The ampoule unit proposed by this disclosure comprises an ampoule for an administering device having a proximal end and a distal end. In this respect, what is referred to as the proximal end of the ampoule is the end of the administering device which is disposed away from the dispensing end when the ampoule is being used. The dispensing end is or can be connected to an injection needle or injection nozzle from which the fluid contained in the ampoule can be administered to a human's or animal's body. Accordingly, the distal end of the ampoule is disposed opposite the proximal end, which can be connected to a needle holder, a needle, or a nozzle in order to use the ampoule or is supplied already connected to one of these elements.

The ampoule may be supplied as an empty unit which is not filled with the fluid until shortly before use. In addition, it may also be supplied to the user already filled if, for example, dispensing is to be performed by a self-administrator.

In one embodiment, the ampoule unit comprises an ampoule which has a thread at least at its proximal end. This thread is preferably formed directly during the process of manufacturing the ampoule such as, for example, in a casting or pressing mold, and is usually made from the same material as the ampoule which may be, for example, glass, metal, porcelain, ceramic, or plastic. However, the part incorporating the thread may also be made from a different material than the rest of the ampoule. If different materials are used, these materials may have similar physical properties such as E-modulus or coefficient of thermal expansion, for example.

This disclosure further relates to an ampoule unit comprising an ampoule and an adapter which can be connected to it so as to be locked in rotation and translation. The adapter may extend beyond the ampoule at least in the proximal direction. Standard, commercially available ampoules may be used with such an ampoule unit by preference. The adapter has a thread and is manufactured separately and then subsequently assembled with the standard ampoule to produce the ampoule unit proposed by the disclosure such as, for example, by bonding or welding. One problem which might occur with bonding is that bits of the adhesive used could dissolve in the fluid contained in the ampoule over time, which might be problematic in terms of supplying filled ampoules over longer periods of time. One advantage of manufacturing the ampoule and adapter separately is that the ampoule body can be produced or purchased without a thread in large quantities, and the parts incorporating the thread can be produced in smaller quantities for different applications, for example, with threads of differing pitch. The requisite second step of assembling the ampoule and threaded part could then take place immediately prior to filling the ampoules or, if supplying empty ampoules, immediately before their delivery to the user.

The adapter has a thread, at least at its proximal end. In principle, a simple nut may be used as an adapter, which is or can be secured onto the proximal end of the ampoule. In this case, the ampoule is preferably a standard, commercially available ampoule body. The adapter may also partially surround the ampoule or extend into the ampoule in the proximal region. Moreover, the adapter may also totally surround the ampoule in the sense that the ampoule can be accommodated inside the adapter. Finally, the adapter may also be fitted directly on the ampoule in a positive fit such as, for example, shrink-fitted or injected on. Alternatively, the connection between the adapter and ampoule may also be releasable, in other words the ampoule can be inserted into the adapter and subsequently removed from the adapter after emptying. In either case, the adapter is not able to move relative to the ampoule and instead the two parts act in unison for every linear movement and every rotating movement. However, the adapter may be separate from the ampoule. For example, it may be provided in the form of an internal thread on the internal face of the housing of the administering device or may be a separate threaded part fixedly connected to the housing which forms the adapter proposed herein.

Embodiments of the ampoule units defined in the claims will be described below and, unless stated otherwise, all embodiments apply to both of the ampoule units proposed by this disclosure.

The ampoule unit may have a plunger unit for dispensing the fluid product. Pressure can be applied to the fluid product via this plunger unit, for example, in order to dispense it from the ampoule and enable it to be injected into a human or animal. To this end, the plunger unit, which comprises a plunger and a plunger rod, for example, has a thread on the plunger or on the plunger rod which forms a complementary thread to the thread of the ampoule unit. The two threads may be engaged, i.e. the plunger unit can be screwed into or onto the proximal end of the ampoule unit. Accordingly, the plunger is introduced into the proximal end of the ampoule and is moved in the forward drive direction by turning it further in the same direction so that it screws into the ampoule.

The plunger of the plunger unit may be made from a material which is sufficiently elastic to provide a seal for the ampoule in the proximal direction and simultaneously afford a slight sliding friction resistance to the material of the internal face of the ampoule. Alternatively or in addition, a separate seal (e.g., a gasket or o-ring) may be attached to the distal plunger face. In order to reduce sliding friction resistance, the plunger may be of a concave shape at its circumference so that the contact region between the plunger and ampoule internal wall is limited to the leading and trailing ends of the plunger in the forward drive direction. However, the plunger may also be made from a hard cylindrical core onto which one or more sealing rings are injected or disposed. The material for the sealing rings may be selected with a goal of obtaining the tight seal and low friction resistance. In order to reduce static and/or sliding friction resistance, the ampoule internal face and/or the plunger external face and the seals may be coated with a substance which reduces friction.

As far as the type of thread of the ampoule unit is concerned, it may be an internal thread or an external thread in principle. In one embodiment, the thread is disposed on the external wall of the ampoule unit (e.g., an external thread). In this case, the plunger unit is shaped so that the complementary thread sits in the thread engagement with the thread disposed on the external face of the ampoule, while a central part of the plunger unit simultaneously causes the fluid product to be dispensed from the ampoule.

In another embodiment, the thread of the ampoule unit may be an internal thread, in which case the plunger unit can be screwed into the ampoule unit from its proximal end. Since the thread in this embodiment is disposed at the proximal end only, the ampoule is closed off by a seal element in the proximal direction, preferably a gasket, which lies in direct contact with a horizontal thread end of the threaded portion projecting out vertically from the ampoule wall. In this embodiment, the gasket has an axial thickness and may be connected to the plunger unit by a positive join, for example, so that it turns with the plunger unit as it is screwed into the ampoule and also serves as a seal element. The gasket may also constitute the plunger of the plunger unit within the meaning of this disclosure.

In general, the thread and complementary thread have a thread pitch of 0 mm to 2 mm and in one embodiment lies between 0.5 mm and 2 mm. Alternatively, the thread pitch may also be in the range of less than 1 mm or more than 2 mm.

The plunger unit, which preferably comprises a single piece, is screwed into the ampoule unit as the thread engagement is established between the plunger unit and ampoule unit in order to dispense the fluid product. In other words, the part of the plunger unit effecting the dispensing operation, namely its front end or, in the case of the external thread solution, the part guided in the ampoule, is screwed about its longitudinal axis into the ampoule unit, which is secured to prevent it from rotating as well. This combined rotating and linear movement of the plunger unit causes the front end of the plunger unit effecting the dispensing action to travel along a spiral-shaped path which is longer than the distance of a purely linear motion, often used in existing designs. However, a longer distance enables the static friction between the ampoule internal face and plunger unit external face to be overcome more readily and switch to a sliding friction.

Due to the fact that the plunger unit is able to move in the ampoule in a manner that is not exclusively linear, the fluid can be more smoothly and efficiently dispensed while simultaneously minimizing the effects of static friction. In order to cause the screwing motion of the plunger unit, it is sufficient for the plunger unit to be simply driven in rotation. The thread engagement between the ampoule and plunger unit shortens the chain of strain in the system compared with conventional solutions, results in a better defined plunger position in the ampoule, and also reduces the accumulating bolus volume and delay times when dispensing. Especially in the case of repeated dispensing of extremely small fluid quantities, this offers greater reliability that the same quantity of fluid will always be dispensed from the ampoule. As a result, the same quantity of fluid such as, for example, a medicament is administered to a user in a reliably reproducible way with each use, which enables the quantity to be dispensed per dispensing operation to be limited to the necessary minimum.

As described, the ampoule unit is provided with a thread at least at the proximal end. However, provision of the thread is not only limited to the proximal end, especially in the case of a solution based on an external thread, and instead, the ampoule unit external face as a whole may be formed as a thread.

The plunger unit may be provided in the form of a plunger solely or as a combination of a plunger and plunger rod. If the plunger unit comprises the plunger and plunger rod, the complementary thread which can be placed in a thread engagement with the thread of the ampoule unit may be provided either on the plunger or on the plunger rod. The plunger and plunger rod may comprise a single piece and, if so, may be made from plastic and manufactured by an injection casting process such as, for example, two-component injection casting. Alternatively, however, the plunger and plunger rod may also be separate parts, which are non-releasably connected to one another, for example by means of a bonded or welded connection. Finally, the plunger may also be releasably connected to the plunger rod, in which case the connection may be a screw or plug-in connection. In this case, however, it is necessary to guarantee that the plunger and plunger rod always rotate in unison about their rotation axis when the plunger unit is being screwed into the ampoule unit. In other words, the plunger must not be able to move relative to the plunger rod in the connected state when the unit comprising the plunger and plunger rod is being screwed into the ampoule unit. The front end of the plunger may form a seal which is formed on the plunger during the manufacturing process or is connected to the plunger so that it is prevented from rotating, for example, by being welded.

However, the plunger unit may also comprise the plunger, a sleeve incorporating the thread fixedly connected to the plunger, and a drive element. The sleeve has a cut-out in the longitudinal direction, for example, a square blind bore, in which the drive element positively engages, in this embodiment, an appropriately designed square bar. When the drive element is driven in rotation, for example via a gear connected to its proximal end, the sleeve and the plunger rotate automatically and are screwed in the dispensing direction due to the threaded connection between the sleeve and ampoule unit.

The ampoule unit may be a disposable unit which is disposed of once it is completely empty. This being the case, it is of advantage for the recycling process if, in the case of the ampoule unit having the fixedly connected thread part, the ampoule and the thread part are made from the same material. In the case where the adapter solution is used, it is advantageous if the adapter can be released from the ampoule for disposal purposes and the two parts can be disposed of and recycled separately from one another.

The ampoule units described above may be used in both stationary and mobile administering devices.

FIG. 1 illustrates one embodiment of an ampoule unit 1 which is connected to a plunger unit 2. The ampoule unit 1 comprises an ampoule 1a and an adapter 4. The ampoule 1a is disposed in and fixedly coupled to an adapter 4 such that the ampoule 1a and the adapter 4 can not move with respect to each other. The ampoule 1a has a distal opening 10 for dispensing the ampoule contents from the fluid chamber 6. The adapter 4 has a proximal opening for accommodating and guiding a displacement unit which, in this embodiment, is the plunger unit 2. The proximal opening of the adapter 4 has adapter threads 4a which are internal threads in this embodiment. The adapter threads 4a are disposed at the most proximal end of the adapter 4 but it may be disposed at a different point of the adapter 4, for example shifted further in the distal direction.

The plunger unit 2 includes the plunger rod 3 and the plunger 2p. The plunger rod 3 has external threads 3a which matingly couple to (i.e., engage with) the adapter threads 4a such that the plunger rod 3 may be screwed into the adapter 4. The plunger rod 3 is also fixedly coupled to the plunger 2p such that both move (i.e., rotationally and linearly) in unison. Rotation of the plunger rod 3 causes it to be screwed into the ampoule 1a thus causing the plunger 2p to rotate and move linearly in the forward direction F of the distal end.

The plunger 2p may have at least one seal 5 which may be rubber or other suitable material. The seal 5 may help prevent the fluid disposed in the ampoule 1a from leaking into the distal end of the ampoule 1a. The seal 5 is fixedly coupled to the plunger 2p such that rotation of the plunger 2p causes the seal 5 to rotate as well. The seal 5 may be fitted already at the time of manufacture of the ampoule 1a, and is driven in the distal direction by the plunger unit 2 during the dispensing operation. In the latter case, the front end of the plunger 2p would also move the seal 5 in the forward drive direction F uniformly. This being the case, the plunger 2p is connected to the seal 5 either by a positive fit or some other connection so that it is locked in rotation, i.e. the seal 5 would rotate with the plunger 2p.

Figure 2:
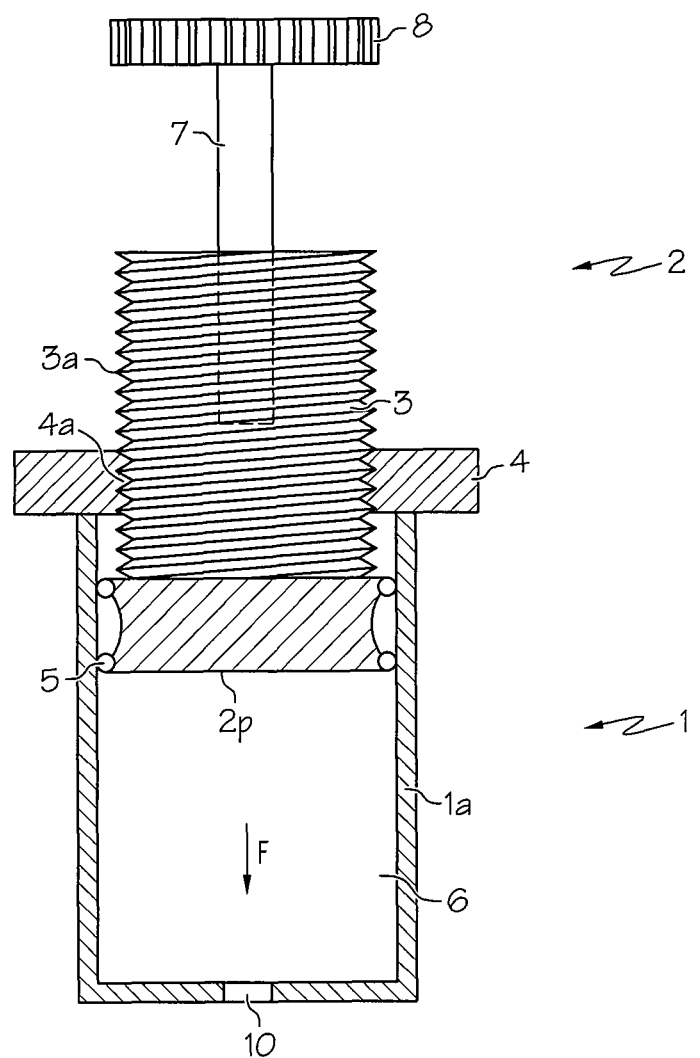
FIG. 2 depicts an ampoule unit according to one or more embodiments shown and described herein.

FIG. 2 illustrates another embodiment of the ampoule unit 1. Fixedly connected to the ampoule 1a is an adapter 4 in the form of a nut with an internal thread 4a. The term fixedly in this context means that the nut or adapter 4 is not able to move relative to the ampoule 1a, either linearly or in rotation. This may be achieved using an appropriate bonded or welded connection but could just as easily be achieved by appropriate shaping of the ampoule end, enabling the adapter 4 to be retained in a positive fit and secured to prevent any relative movement with respect to the ampoule unit 1.

In this embodiment, the plunger 2p is of a concave shape at its external face and has a seal 5 extending around its top and bottom end respectively. The plunger 2p may be made as a separate part and already serve as a rearward seal when the ampoule 1a is delivered to the user. In this case, it has connecting elements at its proximal end, namely that opposite the forward drive direction F, by means of which it can be connected to the plunger rod 3 so that it is locked in rotation. The expression locked in rotation means that, when connected to the plunger rod 3, the plunger 2p and the plunger rod 3 move (i.e., rotational and linear motion) in unison. Thus with every rotation of the plunger rod 3, the plunger 2p is screwed into the ampoule 1a in the distal direction and forces fluid out of the fluid chamber 6 through the opening 10.

The plunger rod 3 has an external thread 3a, which is a complementary thread to the internal thread 4a of the adapter 4. Accordingly, the plunger rod 3 is able to turn with its thread 3a in the thread 4a of the adapter 4 and is thus screwed in the forward drive direction F into the ampoule 1a. The plunger rod 3 may be connected to a gear 8 directly, via a stub (not shown), or via a drive element 7. The gear 8 may be driven by a motor or driven manually so as to screw the plunger 2p in the forward drive direction F.

Figure 3:
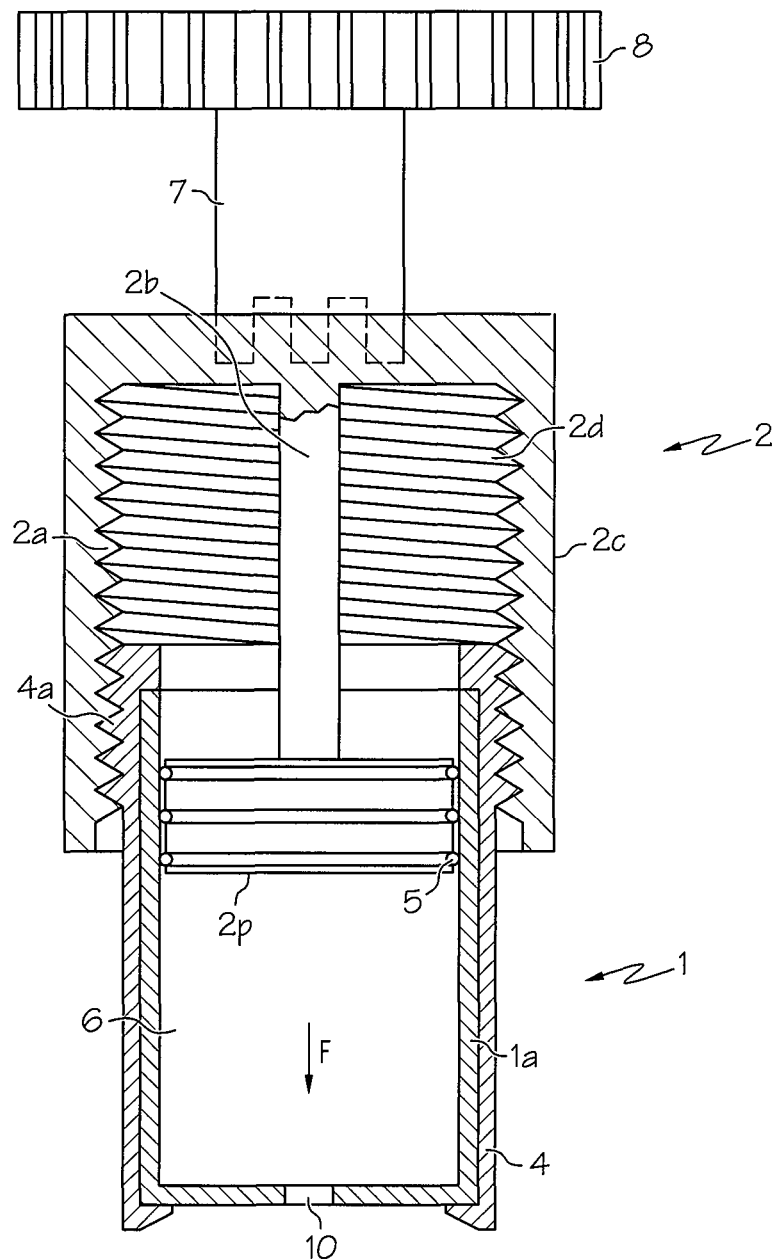
FIG. 3 depicts an ampoule unit according to one or more embodiments shown and described herein.

FIG. 3 depicts another embodiment of the ampoule unit 1. In this embodiment, the ampoule 1a is retained in an adapter 4 which partially surrounds it so that the adapter 4 is not able to move relative to the ampoule 1a, either linearly or in rotation. Accordingly, the adapter 4 may be positively connected to the ampoule 1a, for example, adhered, welded, or shrink-fitted. One important aspect is the rigid connection of the two parts which does not allow any relative movement between the ampoule 1a and adapter 4.

In its rear proximal region, the adapter has an external thread 4a. Disposed in a thread engagement with the adapter 4 is a plunger unit 2. The plunger 2p is connected to the central rod 2b so as to rotate in unison with it and the latter is in turn connected to the plunger sleeve 2c so as to rotate in unison with it. In this embodiment, the central rod 2b and the plunger sleeve 2c may be manufactured as a single piece, for example as an injection cast part. When the plunger sleeve 2c is turned as it is screwed onto the adapter thread 4a by means of the plunger thread 2a, the central rod 2b rotates at the same speed and in the same direction as the plunger sleeve 2c. In this respect, the plunger 2p may either be the front end of the central rod 2b, a separate part which is fixedly connected to the central rod 2b, or the plunger 2p may form the termination of the filled ampoule, in which case it is only when the plunger unit 2a, 2b, 2c has been fitted on the adapter 4 with the plunger unit 2a, 2b, 2c that it causes the plunger 2p to rotate as the plunger unit 2a, 2b, 2c is being screwed onto the ampoule 1a. The plunger 2p may have at least one seal 5, which prevents the fluid from escaping from the ampoule 1a via the plunger 2p.

In order to dispense the contents of the fluid chamber 6, a plunger unit 2 co-operates with the ampoule 1a. This plunger unit 2 comprises a plunger 2p with an external diameter which largely corresponds to the internal diameter of the ampoule 1a. At its foremost distal end, the plunger 2p has a least one seal 5, which prevents the contents of the ampoule 1a from escaping from the ampoule 1a at the rear during the dispensing operation. This seal 5 may be fixedly connected to the plunger 2p but may also serve as the proximal seal of the ampoule 1a and may be fitted already at the time of manufacture of the ampoule 1a, and is driven in the distal direction by the plunger unit 2 during the dispensing operation. In the latter case, the front end of the plunger 2p would also move the seal 5 in the forward drive direction F, preferably uniformly. This being the case, the plunger 2p is connected to the seal 5 either by a positive fit or some other connection so that it is locked in rotation, i.e. the seal 5 would rotate with the plunger 2p. The plunger 2p and plunger rod 2b are surrounded by a plunger sleeve 2c such that the central rod 2b and plunger sleeve 2c jointly form the plunger unit 2 and are preferably manufactured together as a single piece, for example by an injection casting process.

Disposed between the central rod 2b and the plunger sleeve 2c is a slot 2d. While the external face of the plunger 2p is relatively smooth, the internal face of the plunger sleeve 2c is provided in the form of a plunger thread 2a and constitutes a complementary thread to the adapter thread 4a. This means that the plunger unit 2 can be connected to the ampoule unit 1 by establishing a thread engagement between the plunger thread 2a and the adapter thread 4a. In other words, the plunger unit 2 of the embodiment illustrated may be screwed onto the ampoule unit 1. When the plunger unit 2 is screwed onto the ampoule unit 1, the plunger 2p is inserted into the ampoule 1a and, as it moves in the distal direction, it is able to force the contents of the fluid chamber 6 through the opening 10 of the ampoule 1a.

The plunger 2p is not only able to move linearly forward in the ampoule 1a, but also rotates. The plunger 2p can be screwed into the ampoule unit 1 by means of the adapter thread 4a and the complementary thread 2a by a rotating movement of the plunger unit 2. In order to travel a distance X in the forward drive direction F corresponding to a dispensing quantity, the plunger 2p will therefore travel a longer distance as it is screwed into the ampoule 1a than would be the case in the event of a purely linear movement. This advantageously ensures that a static friction between the ampoule internal wall and plunger external face is reliably overcome and converted to a sliding friction during the spiral movement of the plunger 2p. As a result, even if small quantities of fluid are dispensed repeatedly, the pre-set quantity is always dispensed to a high degree of reliability. Any distortion of the individual dispensed quantities due to static friction problems or a long chain of strain within the system is largely eliminated.

Finally, FIG. 4 illustrates another embodiment of the ampoule unit 1. The adapter in this embodiment is provided in the form of a housing 9. This housing 9 may be the housing of the administering device for example, or the housing of a sub-unit of the administering device which is inserted in the administering device as a unit. The thread 9a formed on the internal face of the housing wall lies above an ampoule 1a inserted in the housing. The ampoule 1a is retained in the housing 9 so that it is not able to move in rotation or translation. A thread engagement is established between the internal thread 9a of the housing 9 and the external thread 3a of the plunger rod 3 of the plunger unit 2. When the plunger unit 2 is rotated about its rotation axis, the plunger 2p is screwed in the forward drive direction F into the ampoule 1a and causes a dispensing operation from the fluid chamber 6 through the opening 10. Reference may be made to FIG. 2 for a more detailed description. The description given of how the adapter 4 and plunger rod 3 co-operate also applies to the embodiment illustrated as an example in FIG. 4.

While particular embodiments and aspects have been illustrated and described herein, various other changes and modifications may be made without departing from the spirit and scope of the disclosure. Moreover, although various inventive aspects have been described herein, such aspects need not be utilized in combination. It is therefore intended that the appended claims cover all such changes and modifications that are within the scope of this disclosure.

What is claimed is:

1. An ampoule unit for an administering device, the ampoule unit comprising:
    an ampoule with a distal end with an opening for dispensing a product and a proximal end with an opening for accommodating a displacement unit; and
    an adapter which can be connected to the ampoule such that the distal end of the ampoule is at least partially disposed in the adapter and the adapter is positively connected to the ampoule such that the adaptor is not able to move in rotation or translation relative to the ampoule when connected, wherein
        the adapter comprises a thread which can be placed in a thread engagement with a complementary thread which is part of the displacement unit,
        the displacement unit comprises a plunger unit having the complementary thread to the thread of the adapter,
        the plunger unit comprises a plunger and a plunger rod,
        the plunger is disposed in direct contact with the product when the ampoule is connected to the rest of the ampoule unit, and
        the plunger is unable to move relative to the plunger rod and rotates in conjunction with rotation of the complementary thread to the thread of the adaptor.

2. The ampoule unit as claimed in claim 1, wherein the complementary thread is at least partially formed on the plunger unit which can be matingly engaged with the thread of the adapter.

3. The ampoule unit as claimed in claim 2, wherein the complementary thread is disposed on the plunger or the plunger rod.

4. The ampoule unit as claimed in claim 3, wherein the plunger is releasably connected to the plunger rod by means of a screw or plug-in connection.

5. The ampoule unit as claimed in claim 3, wherein the plunger is non-releasably connected to the plunger rod.

6. The ampoule unit as claimed in claim 5, wherein the plunger and the plunger rod are made as a single piece.

7. The ampoule unit as claimed in claim 3, wherein the plunger or the plunger rod is configured to be connected to a drive which drives the plunger and the plunger rod in rotation.

8. The ampoule unit as claimed in claim 2, wherein the plunger unit is configured to rotate about a rotation axis relative to the ampoule due to the thread engagement and is thus moved in the ampoule in a screwing action in a direction of the distal end.

9. The ampoule unit as claimed in claim 1, wherein a thread pitch of the thread and the complementary thread are less than 2 mm.

10. The ampoule unit as claimed in claim 1, wherein a thread pitch of the thread and the complementary thread is in a range of 0.5 mm to 2 mm.

11. The ampoule unit as claimed in claim 1, wherein the thread is an internal thread and the complementary thread is an external thread or vice versa.

12. The ampoule unit as claimed in claim 1, wherein the adapter is releasably connected to the ampoule.

13. The ampoule unit as claimed in claim 1, wherein the adapter is non-releasably connected to the ampoule.

14. The ampoule unit as claimed in claim 13, wherein the adapter is injected or shrink-fitted onto the ampoule.

15. The ampoule unit as claimed in claim 1, wherein the adapter is a part of a housing of the ampoule or a part of a housing of the administering device.

16. The ampoule unit as claimed in claim 1, wherein the ampoule unit is configured to be disposed of once the ampoule unit is completely empty.

* * * * *